US010112061B2

(12) United States Patent
Molenda

(10) Patent No.: US 10,112,061 B2
(45) Date of Patent: Oct. 30, 2018

(54) COSMETIC COMPOSITION FOR HAIR AND SCALP

(75) Inventor: Michael Molenda, Frankfurt (DE)

(73) Assignee: KAO GERMANY GMBH, Darmstadt (DE)

( * ) Notice: Subject to any disclaimer, the term of this patent is extended or adjusted under 35 U.S.C. 154(b) by 669 days.

(21) Appl. No.: 13/132,228

(22) PCT Filed: Dec. 9, 2009

(86) PCT No.: PCT/EP2009/008772

§ 371 (c)(1), (2), (4) Date: Jun. 1, 2011

(87) PCT Pub. No.: WO2010/069501

PCT Pub. Date: Jun. 24, 2010

(65) Prior Publication Data

US 2011/0232670 A1 Sep. 29, 2011

(30) Foreign Application Priority Data

Dec. 15, 2008 (EP) .................................... 08021709

(51) Int. Cl.

| | |
|---|---|
| ***A61Q 5/12*** | (2006.01) |
| ***A61K 8/02*** | (2006.01) |
| ***A61K 8/19*** | (2006.01) |
| ***A61K 8/20*** | (2006.01) |
| ***A61K 8/36*** | (2006.01) |
| ***A61K 8/41*** | (2006.01) |

(52) U.S. Cl.

CPC .................. *A61Q 5/12* (2013.01); *A61K 8/02* (2013.01); *A61K 8/19* (2013.01); *A61K 8/20* (2013.01); *A61K 8/36* (2013.01); *A61K 8/416* (2013.01); *A61K 2800/244* (2013.01); *A61K 2800/88* (2013.01)

(58) Field of Classification Search

None

See application file for complete search history.

(56) References Cited

U.S. PATENT DOCUMENTS

| | | | | |
|---|---|---|---|---|
| 2,305,356 | A * | 12/1942 | Luckenbach | 132/202 |
| 4,507,278 | A * | 3/1985 | DeMarco | A61K 8/22 424/62 |
| 5,447,654 | A * | 9/1995 | Millequant et al. | 252/186.25 |
| 5,783,175 | A * | 7/1998 | Schultz et al. | 424/62 |
| 6,302,920 | B1 * | 10/2001 | Lorenz et al. | 8/111 |
| 6,540,791 | B1 * | 4/2003 | Dias | 8/111 |
| 6,596,035 | B2 * | 7/2003 | Gutkowski et al. | 8/405 |
| 2005/0097683 | A1 * | 5/2005 | Nocker et al. | 8/405 |
| 2005/0257335 | A1 * | 11/2005 | Dumousseaux | A61K 8/11 8/406 |
| 2008/0087294 | A1 * | 4/2008 | Glenn | A45D 19/0008 132/221 |

FOREIGN PATENT DOCUMENTS

| | | | | |
|---|---|---|---|---|
| EP | 1 197 205 A | | 4/2002 | |
| EP | 2055296 | * | 5/2009 | A61K 8/22 |
| WO | 2003/047641 A | | 6/2003 | |
| WO | 2007/075207 A | | 7/2007 | |

OTHER PUBLICATIONS

Redken Pro-Oxide Cream Developer vol. 20. http://www.socialgrocery.com/products/Redken-5th-Avenue-NYC/Pro-oxide-Cream-Developer-Volume-20. Published 2013.*

Pro-Oxide Cream Developer. http://web.archive.org/web/20080222212437/http://www.extendedlengths.com/reprcrde.html. Published: Feb. 22, 2008.*

Hair Talk. http://talk.hairboutique.com/forum_posts.asp?TID=63207. Published: Dec. 2, 2008.*

Ecolor line. http://helensewardus.freeservers.com/ecolor_line.htm. Published: Feb. 12, 2007.*

The Hair Care Market. http://www.thefreelibrary.com/The+hair+care+market%3A+hair+care+will+never+go+out+of+style+with+the...-a081009075. Published Dec. 1, 2001.*

Redken Shades. http://www.behindthechair.com/forum/displaythread.aspx?DID=2082. Published Apr. 13, 2004.*

Creams & Lotions. http://web.archive.org/web/20101127190412/http://www.phytoclinic.com/phyto-pharmacy/creams-lotions.html. Published: Nov. 27, 2010.*

The Guide to Healthy Hair. http://www.cnn.com/2007/LIVING/homestyle/11/27/healthy.hair/. Published: Nov. 27, 2007.*

Killer Strands Hair Clinic. http://killerstrands.blogspot.com/2007/09/bleach-for-stars-cont.html. Published: Sep. 17, 2007.*

International Search Report dated Mar. 19, 2010.

* cited by examiner

*Primary Examiner* — Jyothsna A Venkat

(74) *Attorney, Agent, or Firm* — Norris McLaughlin P.A.

(57) ABSTRACT

Present invention relates to a cosmetic composition for hair and scalp obtained by mixing two compositions wherein the one is a water soluble powder and the other is an aqueous composition comprising at least one hair and scalp conditioning compound. The object of the present invention is a two-part composition for hair and scalp wherein first part is a substantially non-aqueous composition comprising at least one water soluble salt with an endothermic dissolving enthalpy of 5 kJ/mol or more and a second part is an aqueous composition comprising at least one hair conditioning compound.

12 Claims, No Drawings

COSMETIC COMPOSITION FOR HAIR AND SCALP

This application is a 371 application of PCT/EP2009/008772 filed Dec. 9, 2009, which claims foreign priority benefit under 35 U.S.C. § 119 of European Application No. 08021709.4 filed Dec. 15, 2008.

Present invention relates to a cosmetic composition for hair and scalp obtained by mixing two compositions wherein the one is a water soluble powder and the other is an aqueous composition comprising at least one hair and scalp conditioning compound.

Hair and scalp compositions especially known as scalp lotions have been used regularly either for refreshing or reducing certain irritation on the scalp. These compositions are so formulated that they are not rinsed off from hair and scalp after application. They comprise often alcohol which when applied onto hair gives a kind or refreshed feeling. At the same time, menthol or menthol lactylate comprising compositions with or without alcohol are known on the market.

The problem encountered with the known compositions is that in order to realize better refreshed feeling on the scalp relatively high concentration of alcohol and/or menthol is needed which often turns into higher scalp irritation.

The present invention starts from the above mentioned problem and aims at providing compositions with improved refreshing effect and at the same time less irritant to scalp and having excellent hair conditioning effect so that hair is easier to comb, has better shine, feels softer upon touching, has especially higher volume and body and easier to style.

Inventors of the present invention has surprisingly found out that a two part composition wherein first part a substantially non-aqueous composition comprising at least one water soluble salt with an endothermic dissolving enthalpy of 5 kJ/mol or more and second part which is an aqueous composition comprising at least one hair conditioning compound refreshes and conditions scalp and hair excellently so that scalp does not feel stressed and hair is excellently conditioned and has improved cosmetic properties.

Accordingly, the first object of the present invention is a two-part composition for hair and scalp wherein first part is a substantially non-aqueous composition comprising at least one water soluble salt with an endothermic dissolving enthalpy of 5 kJ/mol or more and a second part is an aqueous composition comprising at least one hair conditioning compound.

Further object of the present invention is a process for conditioning hair and scalp wherein first and second compositions are mixed immediately prior to application onto optionally shampooed hair and scalp and not rinsed of from hair and scalp, wherein the first part is a substantially non-aqueous composition comprising at least one water soluble salt with an endothermic dissolving enthalpy of 5 kJ/mol or more and second part is an aqueous composition comprising at least one hair conditioning compound.

Another object of the present invention is the use of the two part composition of the present invention for conditioning hair and scalp, especially for refreshing scalp and improving hair properties in terms of combability, shine, soft feeling upon touching, volume, body and easy to style.

With the term substantially non-aqueous composition it is meant that the composition does not include any added water, wherein the crystal water included in the compounds are excluded.

First part of the composition is a substantially non-aqueous composition comprising at least one water soluble salt with a dissolving enthalpy of 5 kJ/mole or more, preferably 7.5 kJ/mol or more and more preferably 10 kJ/mol or more. Concentration of at least one water soluble salt is at least 40%, preferably in the range of 50 to 100%, more preferably 60 to 100% and most preferably 70 to 100% by weight calculated to total of first part composition.

Suitable non-limiting examples are sodium acetate trihydrate, potassium chloride, potassium bromide, potassium iodide, ammonium chloride, ammonium bromide, ammonium iodide, ammonium nitrate, silver chloride, silver carbonate, silver nitrate, calcium fluoride, calcium chloride hexahydrate, and sodium carbonate decahydrate. Preferred are sodium acetate trihydrate, potassium chloride, potassium bromide, potassium iodide, ammonium chloride, ammonium bromide, ammonium iodide, calcium chloride hexahydrate, and sodium carbonate decahydrate. More preferred are sodium acetate trihydrate, potassium chloride, potassium bromide, ammonium chloride, ammonium bromide, calcium chloride hexahydrate, and sodium carbonate decahydrate. Most preferred are sodium acetate trihydrate, potassium chloride, ammonium chloride, calcium chloride hexahydrate, and sodium carbonate decahydrate.

Substantially non-aqueous first part composition can comprise additionally powder substances which are water soluble or readily dispersible which allows directly application onto scalp and hair. Non-limiting examples are UV filters mentioned below, any powder surfactant compound, dyestuffs, physical UV filters, etc.

In a preferred embodiment of the present invention first part composition comprises synthetic mica coated with metal oxide or oxides having a volume particle size distribution in the range of 1 to 750 μm. Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail. The content of the document is included herewith by reference.

Suitable metal oxide or oxides for coating synthetic mica are titanium dioxide, chromium oxide, ferric oxide or mixtures thereof. In the present invention the preferred is synthetic mica coated with titanium dioxide. Such materials are commercially available from Sun Chemical Corporation and Merck (Timiron Synwhite 40) and known with their INCI names Synthetic Fluorphologopite The volume particle size distribution of synthetic mica coated with a metal oxide or oxides is in the range of 1 to 750 μm, preferably 1 to 250 μm, more preferably 1 to 100 μm and most preferably 5 to 95 μm. The particle sizes referred are relating to the volume particle size distribution meaning that particles found in the coated synthetic mica having volume particle size in the given ranges.

Concentration of synthetic mica coated with at least metal oxide or oxides is from 0.01 to 5%, preferably 0.1 to 4%, more preferably 0.2 to 3% and most preferably 0.2 to 2% by weight calculated to total of first part composition.

The second part composition is an aqueous composition and comprises at least one conditioning agent. Conditioning agent is preferably selected from oily substances, cationic amphiphilic ingredients, cationic polymers or their mixtures.

Oily substances are selected from such as silicone oils, either volatile or non-volatile, natural and synthetic oils. Among silicone oils those can be added to the compositions include dimethicone, dimethiconol, polydimethylsiloxane, DC fluid ranges from Dow Corning, arylated silicones such as phenyl trimethicone or any other silicone with up to 5 aryl, preferably phenyl, group in its molecule, natural oils such as olive oil, almond oil, avocado oil, wheatgerm oil, ricinus oil and the synthetic oils, such as mineral oil, fatty acid alkyl esters such as isopropyl myristate, palmitate, stearate and isostearate, oleyl oleate, isocetyl stearate, hexyl laurate, dibutyl adipate, dioctyl adipate, myristyl myristate and oleyl erucate.

Substantially non-aqueous second composition of the present invention may comprise at least one dialkyl carbonate of general formula

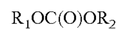

where $R_1$ and $R_2$ are independent from each other linear or branched saturated alkyl chains with 6 to 22 C atoms as an oily component.

Preferred at least one dialkyl carbonate is selected from di(caprylyl) carbonate and di(ethylhexyl) carbonate.

In case that the second composition comprises one or ore oily substances, it can also be in the form of a two phase composition which has optically separated oil and aqueous phases.

Oily ingredients mentioned above are included in the second composition at a concentration of 0.01 to 50%, preferably 0.05 to 40%, more preferably 0.1 to 35% and most preferably 0.2 to 30% by weight calculated to total of second composition. It should be noted that lower concentrations are especially suitable when second composition is a homogeneous composition and higher concentrations are especially suitable in case that the second composition is two phase composition mentioned above.

Further, second composition can comprises one or more cationic polymers as conditioning agent. Suitable cationic polymers are those of best known with their CTFA category name Polyquaternium. Typical examples of those are Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

It has further been found out that especially those of cationic cellulose type polymers known as Polymer JR type from Amerchol such as Polyquaternium 10 or cationic galactomannans such as cationic guar gum known with trade name Jaguar from Rhône-Poulenc which are chemically for example Guar hydroxypropyl trimonium chloride and cationic tara gum an its derivatives known with INCI name *Caesalpinia spinosa* hydroxypropyltrimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, cationic *Caesalpinia spinosa* gum derivatives, polyquaternium 6, polyquaternium 7, polyquaternium 67 and polyquaternium 70.

The cationic polymers also include the quaternized products of graft polymers from organopolysiloxanes and polyethyl oxazolines described in EP-A 524 612 and EP-A 640 643.

Cationic polymers are included in the second composition at a concentration in the range of 0.01 to 2.5% by weight calculated to total of second composition.

In preferred embodiment of the present invention second part composition comprises at least one cationic and/or cationizable compound of the following general structures

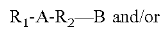

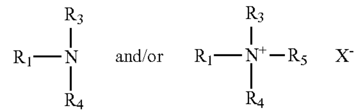

wherein $R_1$ is a straight or branched, saturated or unsaturated alkyl with 8 to 24 C atoms, A is O or

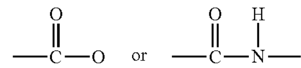

$R_2$ is straight or branched alkyl group with 1 to 4 C atoms which may be substituted with 1 or 2 hydroxyl groups, and B is

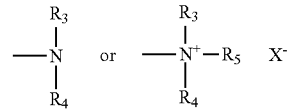

$R_3$, $R_4$ and $R_5$ are same or different H or alkyl with 1 to 4 C atoms which may be substituted with 1 or 2 hydroxyl group, and $R_5$ is in addition $—R_2\text{-}A\text{-}R_1$ and, X is chloride, bromide, methosulfate or any other cosmetically acceptable anion.

In the preferred embodiment of the present invention, $R_1$ is a straight or branched, saturated or unsaturated alkyl with 12 to 22 C atoms, $R_2$ is straight or branched alkyl group with 2 to 3 C atoms which may be substituted with 1 or 2 hydroxyl groups, $R_3$, $R_4$ and $R_5$ are same or different alkyl chain with 1 to 3 C atoms which may be substituted with 1 or 2 hydroxyl group, $R_5$ is in addition $$—R_2\text{-}A\text{-}R_1$$

wherein the here above mentioned preferred alkyl chains apply and, X is chloride, bromide, methosulfate.

More preferably, $R_1$ is a straight or branched, saturated or unsaturated alkyl with 12 to 22 C atoms, $R_2$ is straight or branched alkyl group with 2 to 3 C atoms which may be substituted with 1 or 2 hydroxyl groups, $R_3$, $R_4$ and $R_5$ are same or different alkyl chain with 1 to 3 C atoms which may be substituted with 1 or 2 hydroxyl group, $R_5$ is in addition $$—R_2\text{-}A\text{-}R_1$$

wherein the here above mentioned preferred alkyl chains apply, A is

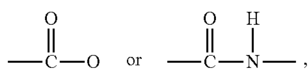

B is

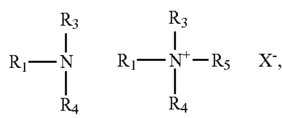

and

X is chloride, bromide, methosulfate.

Most preferably $R_1$ is a straight or branched, saturated or unsaturated alkyl with 12 to 22 C atoms, $R_2$ is straight or branched alkyl group with 2 to 3 C atoms which may be substituted with 1 or 2 hydroxyl groups, $R_3$, $R_4$ and $R_5$ are same or different alkyl chain with 1 to 3 C atoms which may be substituted with 1 or 2 hydroxyl group, $R_5$ is in addition $$—R_2\text{-}A\text{-}R_1$$

wherein the here above mentioned preferred alkyl chains apply, A is

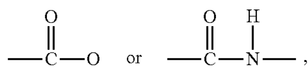

B is

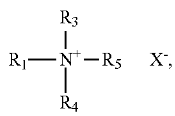

and

X is chloride, bromide, methosulfate.

Non-limiting suitable examples are cetyltrimethyl ammonium chloride, steartrimonium chloride, behentrimonium chloride, stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl methylamine, stearamidopropyl diethylamine, stearamidopropyl dibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Preferred are cetyltrimethyl ammonium chloride, steartrimonium chloride, behentrimonium chloride, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, stearamidopropyl amine, stearamidopropyl methylamine, stearamidopropyl diethylamine, stearamidopropyl dibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

More preferred are cetyltrimethyl ammonium chloride, steartrimonium chloride, behentrimonium chloride, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Most preferred are cetyltrimethyl ammonium chloride, steartrimonium chloride, behentrimonium chloride, palmitoamidopropyl trimethyl ammonium chloride, stearamidopropyl trimethylammonium chloride, behenamidopropyl tri hydroxyethalmonium chloride, palmitylpropyl trimethyl ammonium chloride, stearylpropyl trimethylammonium chloride, and behenylpropyl tri hydroxyethalmonium chloride.

Concentration of at least one cationic or cationizable compound according to above given structures is in the range of 0.01 to 20%, preferably 0.02 to 15%, more preferably 0.05 to 12.5% and most preferably 0.1 to 10% and in particular 0.1 to 7.5% by weight calculated to total of second part composition.

The composition according to the present invention can contain organic solvent. Examples of such organic solvents are benzyloxy ethanol, benzyl alcohol, phenoxy ethanol, phenoxy isopropanol, methyl phenoxy ethanol, benzyl glycerol, N-benzyl formide, N-methylpyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.5% to 10%, preferably 0.5-5% by weight calculated to the total of second part composition.

The second composition may contain active ingredients such as moisturisers, sequestering agents, UV filters and natural ingredients.

The moisturizing agents are selected from panthenol, polyols, such as glycerol, polyethylene glycols with molecular weight 200 to 20,000. The moisturizing ingredients can be included in the conditioner compositions at a concentration range of 0.01-2.5% by weight calculated to the total composition.

The sequestering agents are preferably selected from polycarboxy acids. The preferred one is ethylene diamine tetraacetic acid, EDTA. Typical useful concentration range for sequestering agents is of 0.01-2.5% by weight calculated to the total composition.

The UV filters are that of oil and water soluble ones for the purpose of protecting hair. In other words, anionic and nonionic, oily, UV filters are suitably used in the compositions of the present invention. Suitable UV-absorbing substances is are: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzophenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof, 3-(4'-methyl benzylidene)-DL-campher, and/or polysilicone-15. The amount of the UV-absorber ranges typically from about 0.01% to 5%, more preferably from 0.05% to 3% by weight, calculated to the total of second composition. As mentioned above, water soluble UV filters may also be comprised at the above mentioned concentration ranges in the substantially non-aqueous first composition.

Solubilizers may be added to the compositions especially when oily substances are chosen as conditioning agents and fragrance oils with highly lipophilic properties. Typical solubilizers may be hydrogenated castor oil known with the trade mark Cremophor CO series from BASF. Typical concentration of the solubilizers can be in the range of 0.01-2% by weight, preferably 0.1-1% by weight, calculated to total composition.

Natural plant extracts are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, various "Extrapone®" products, and "Herbasol®". Extracts and the preparation thereof are also described in "Hagers Handbuch der pharmazeutischen Praxis", 4$^{th}$ Ed.

Further second part composition comprises at least one styling polymer selected from anionic, non-ionic, cationic and amphoteric polymers.

These may be nonionic polymers, preferably alcohol- and/or water-soluble vinyl pyrrolidone polymers, such as a vinyl pyrrolidone homopolymers or copolymers, in particular with vinyl acetate. Useful vinyl pyrrolidone polymers are, e.g., those known by the trade name "Luviskol®", for example, the homopolymers "Luviskol® K 30, K 60 and K 90", as well as the water- or alcohol-soluble copolymers from vinyl pyrrolidone and vinyl acetate, distributed by BASF AG under the trade name "Luviskol® VA 55 respectively VA 64". Further possible nonionic polymers are vinyl pyrrolidone/vinyl acetate/vinyl propionate copolymers such as "Luviskol® VAP 343", vinyl pyrrolidone/(meth)acrylic acid ester copolymers, as well as chitosan derivatives.

Amphoteric polymers are found to be useful in composition of the present invention. They are incorporated alone or in admixture with at least one additional cationic, nonionic or anionic polymer, particularly copolymers of N-octyl acrylamide, (meth)acrylic acid and tert.-butyl aminoethyl methacrylate of the type "Amphomer®"; copolymers from methacryl oylethyl betaine and alkyl methacrylates of the type "Yukaformer®", e.g., the butyl methacrylate copolymer "Yukaformer® Am75"; copolymers from monomers containing carboxyl groups and sulphonic groups, e.g., (meth)acrylic acid and itaconic acid, with monomers such as mono- or dialkyl amino alkyl(meth)acrylates or mono- or dialkyl aminoalkyl(meth)acrylamides containing basic groups, in particular amino groups; copolymers from N-octyl acrylamide, methyl methacrylate, hydroxypropyl methacrylate, N-tert.-butyl aminoethyl methacrylate and acrylic acid, as well as the copolymers known from U.S. Pat. No. 3,927,199, are applicable.

Styling polymers are included in the second part composition in the range of 0.1 to 5% by weight calculated to total composition.

Aqueous second part composition has preferably a pH in the range of 3 to 8, preferably 3 to 7, more preferably 3.5 to 6 and most preferably 4 to 5.5. pH is adjusted with known organic and/or inorganic acids and bases.

Consistency of the aqueous second part composition must in principle allow mixing and quick dissolving of the first part substantially non-aqueous composition in it by moderate to strong shaking. Therefore, aqueous second part composition has preferably a viscosity lower than 1,000 mPa·s, preferably lower 800 mPa·s, more preferably 700 mPa·s and most preferably 500 mPa·s measured at 20° C. with a Brookfield viscosimeter with a suitable spindle and speed.

Composition of the present invention can be made available for use in two separate packaging as well as can be packed into a two-chamber packaging which is commercially available. Accordingly further object of the present invention is a product for conditioning hair and scalp which is packed into a two-chamber vessel wherein first chamber contains the first part composition as mentioned above and the second chamber contains the second part composition.

Composition of the present invention is especially suited after a chemical hair dressing service such as colouration, bleaching and permanent shaping. Accordingly another object of the present invention process for treating hair and/or scalp wherein hair is firstly chemically treated and afterwards a two part composition according to present invention is applied onto hair and scalp and dried without rinsing off.

Composition of the present invention can be offered in a kit in combination with any composition for hair and/or scalp. In other words, a kit may comprise in addition to the composition of the present invention, a cleansing composition and/or a conditioning composition or one or more hair colouring compositions, one or more hair bleaching composition and one or more permanent shaping compositions for hair.

Following examples are to illustrate the invention, but not to limit.

EXAMPLE 1

| First part | |
|---|---|
| Sodium acetate trihydrate | 2.5 g |
| Second part | |
| Cetrimonium chloride | 1.0 g |
| Citric acid | to pH 5 |
| Preservative, fragrance | q.s. |
| PEG-60 hydrogenated castor oil | 0.2 g |
| Water | q.s. to 20 g |

The above two compositions were mixed and was shaken until the first part was completely dissolved and immediately afterwards applied onto freshly shampooed wet scalp and hair. It was reported that scalp felt refreshed, and hair was well combable and felt soft upon touching.

EXAMPLE 2

| First part | |
|---|---|
| Sodium acetate trihydrate | 2.5 g |
| Benzophenone-4 | 0.05 g |
| Second part | |
| Behentrimonium chloride | 1.0 g |
| Panthenol | 0.2 g |

-continued

| | |
|---|---|
| Green tea extract | 0.2 g |
| Ethanol | 1.0 g |
| Citric acid | to pH 5 |
| Preservative, fragrance | q.s. |
| PEG-60 hydrogenated castor oil | 0.2 g |
| Water | q.s. to 20 g |

The above two compositions were mixed and was shaken until the first part was completely dissolved and immediately afterwards applied onto freshly shampooed wet scalp and hair. It was reported that scalp felt refreshed, and hair was well combable, felt soft upon touching, had elasticity and body.

EXAMPLE 3

| First part | |
|---|---|
| Calcium chloride hexahydrate | 2.5 g |
| Second part | |
| Behentrimonium chloride | 1.0 g |
| Panthenol | 0.2 g |
| Benzophenone-3 | 0.1 g |
| Green tea extract | 0.2 g |
| Ethanol | 1.0 g |
| Citric acid | to pH 5 |
| Preservative, fragrance | q.s. |
| PEG-60 hydrogenated castor oil | 0.2 g |
| Water | q.s. to 20 g |

The above two compositions were mixed and was shaken until the first part was completely dissolved and immediately afterwards applied onto freshly shampooed wet scalp and hair. It was reported that scalp felt refreshed, and hair was well combable, felt soft upon touching, had elasticity and body.

EXAMPLE 3

| First part | |
|---|---|
| Sodium carbonate decahydrate | 3 g |
| Second part<br>Oil phase | |
| Dimethicone 1 cSt | 3.0 g |
| Almond oil | 0.01 g |
| Phenyl trimethicone | 0.1 g |
| Behentrimonium chloride | 0.5 g |
| Glycerine | 0.4 g |
| Ethyl hexyl methoxy cinnamate | 0.1 g |
| Grape extract | 0.2 g |
| Ethanol | 1.0 g |
| Citric acid | to pH 6 |
| Preservative, fragrance | q.s. |
| PEG-60 hydrogenated castor oil | 0.2 g |
| Water | q.s. to 20 g |

The second part of the above composition was a two-phase composition. The above two compositions were mixed and was shaken until the first part was completely dissolved and immediately afterwards applied onto freshly coloured hair onto wet scalp and hair. It was reported that scalp felt refreshed and soothed, and hair was well combable, felt soft upon touching, had elasticity and excellent shine.

The invention claimed is:

1. A two-part composition for conditioning hair and/or scalp, the two-pan composition comprising:

a substantially non-aqueous first part composition consisting of a water soluble salt; and an aqueous second part composition comprising at least one hair conditioning compound comprising at least one oily substance selected from the group consisting of silicone oils, natural oils and synthetic oils present at a concentration of 0.2% to 30% based on the total composition of the second part composition, wherein the water soluble salt is present at a concentration of between 70% to 100%, based on the total composition of the first part composition, the water soluble salt is selected from the group consisting of sodium acetate trihydrate, calcium chloride hexahydrate, and sodium carbonate decahydrate.

2. The two-part composition according to claim 1, wherein the second part composition comprises at least one cationic and/or a cationizable compound of the following general structures $R_1$-A-$R_2$—B and/or

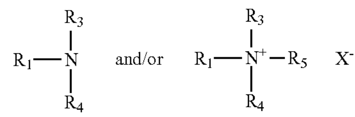

wherein $R_1$ is a straight or branched, saturated or unsaturated alkyl with 8 to 24 carbon atoms, A is O or

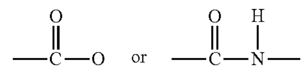

$R_2$ is straight or branched alkyl group with 1 to 4 carbon atoms which may be substituted with 1 or 2 hydroxyl groups, and B is

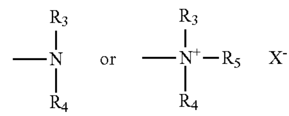

$R_3$, $R_4$ and $R_5$ are same or different H or alkyl with 1 to 4 carbon atoms which may be substituted with 1 or 2 hydroxyl group, and $R_5$ is in addition

—$R_2$-A-$R_1$ and, X is chloride, bromide, methosulfate or any other cosmetically acceptable anion.

3. The two-part composition according to claim 2, wherein at least one cationic and/or a cationizable compound in the second part composition is selected from compounds according to general structure given in claim 2 wherein $R_1$ is a straight or branched, saturated or unsaturated alkyl with 12 to 22 carbon atoms, $R_2$ is straight or branched alkyl group with 2 to 3 carbon atoms which may be substituted with 1 or 2 hydroxyl groups, $R_3$, $R_4$ and $R_5$ are same or different alkyl chain with 1 to 3 carbon atoms which may be substituted with 1 or 2 hydroxyl group, $R_5$ is in addition

—$R_2$-A-$R_1$ wherein, A is

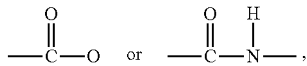

B is

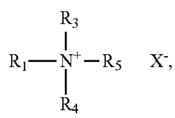

and

X is chloride, bromide, or methosulfate.

4. The two-part composition according to claim 1, wherein the second part composition further comprises at least one UV filter.

5. The two-part composition according to claim 1, wherein the second part composition further comprises at least one cationic polymer.

6. The two-part composition according to claim 1, wherein the second part composition further comprises fatty acid alkyl esters and di alkyl carbonate.

7. The two-part composition according to claim 1, wherein the second part composition further comprises at least one organic solvent.

8. The two-part composition according to claim 1, wherein the second part composition further comprises at least one moisturizing agent selected from panthenol, and polyol.

9. The two-part composition according to claim 1, wherein the second part composition further comprises at least one styling polymer.

10. A process for treating hair and/or scalp, the process comprising:

chemically treating or shampooing the hair and/or the scalp;

applying the two-part composition according to claim 1 onto the hair and/or the scalp after mixing the first part composition and second part composition together; and drying the hair and/or the scalp without rinsing the two-pan composition off the hair and/or the scalp.

11. The two-part composition according to claim 1, wherein the water soluble salt is sodium acetate trihydrate present at a concentration of at least 98%, based on the total composition of the first part composition.

12. A two-part composition for conditioning hair and/or scalp, the two-part composition comprising:

a substantially non-aqueous first part composition consisting of water soluble salt and UV filters present at a concentration of 0.01% to 2%, based on the total composition of the first part composition; and an aqueous second part composition comprising at least one hair conditioning compound comprising at least one oily substance selected from the group consisting of silicone oils, natural oils and synthetic oils present at a concentration of 0.2% to 30% based on the total composition of the second part composition, wherein the at least water soluble salt is present at a concentration of between 70% to 100%, based on the total composition of the first part composition, and the water soluble salt is selected from the group consisting of sodium acetate trihydrate, calcium chloride hexahydrate, and sodium carbonate decahydrate.

* * * * *